United States Patent
Zemlok et al.

(10) Patent No.: US 10,327,771 B2
(45) Date of Patent: *Jun. 25, 2019

(54) POWERED SURGICAL INSTRUMENT

(71) Applicant: Covidien LP, Mansfield, MA (US)

(72) Inventors: Michael A. Zemlok, Prospect, CT (US); Stanislaw Marczyk, Stratford, CT (US); Adam J. Ross, Prospect, CT (US); Russell Pribanic, Roxbury, CT (US)

(73) Assignee: Covidien LP, Mansfield, MA (US)

( * ) Notice: Subject to any disclaimer, the term of this patent is extended or adjusted under 35 U.S.C. 154(b) by 411 days.

This patent is subject to a terminal disclaimer.

(21) Appl. No.: 15/179,554

(22) Filed: Jun. 10, 2016

(65) Prior Publication Data

US 2016/0278772 A1 Sep. 29, 2016

Related U.S. Application Data

(63) Continuation of application No. 14/206,308, filed on Mar. 12, 2014, now Pat. No. 9,364,226, which is a
(Continued)

(51) Int. Cl.
*A61B 17/072* (2006.01)
*A61B 17/068* (2006.01)
(Continued)

(52) U.S. Cl.
CPC ...... *A61B 17/07207* (2013.01); *A61B 17/068* (2013.01); *A61B 17/0643* (2013.01);
(Continued)

(58) Field of Classification Search
CPC ............ A61B 17/07207; A61B 17/068; A61B 17/282; A61B 18/20; A61B 18/1445;
(Continued)

(56) References Cited

U.S. PATENT DOCUMENTS

| | | |
|---|---|---|
| 4,463,759 A | 8/1984 | Garito et al. |
| 4,732,149 A | 3/1988 | Sutter |

(Continued)

FOREIGN PATENT DOCUMENTS

| | | |
|---|---|---|
| EP | 1 769 754 A1 | 4/2007 |
| EP | 1943958 A1 | 7/2008 |

(Continued)

OTHER PUBLICATIONS

Extended European Search Report from counterpart European Application No. 10250228.3 dated Jun. 1, 2010.
(Continued)

*Primary Examiner* — Nathaniel C Chukwurah

(57) ABSTRACT

A powered surgical apparatus, which is configured to engage tissue includes a handle assembly having proximal and distal portions, a movable portion operatively connected to the distal portion of the handle assembly, a tool assembly operatively coupled to the movable portion, a power source configured to supply electrical power, and a transmission system operatively associated with the power source. The movable portion is movable with respect to the handle assembly. The tool assembly is adapted to engage tissue. The transmission system is configured to transmit electrical power or signals between the handle assembly and the movable portion.

18 Claims, 6 Drawing Sheets

Related U.S. Application Data continuation of application No. 12/689,386, filed on Jan. 19, 2010, now Pat. No. 8,708,211.

(60) Provisional application No. 61/152,051, filed on Feb. 12, 2009.

(51) Int. Cl.
| | |
|---|---|
| *A61B 17/28* | (2006.01) |
| *A61B 17/064* | (2006.01) |
| *A61B 17/10* | (2006.01) |
| *A61B 18/14* | (2006.01) |
| *A61B 18/20* | (2006.01) |
| *A61B 17/00* | (2006.01) |
| *A61B 18/00* | (2006.01) |

(52) U.S. Cl.
CPC ........... *A61B 17/10* (2013.01); *A61B 17/282* (2013.01); *A61B 18/1445* (2013.01); *A61B 18/20* (2013.01); *A61B 2017/00022* (2013.01); *A61B 2017/00221* (2013.01); *A61B 2017/00398* (2013.01); *A61B 2017/00734* (2013.01); *A61B 2017/07271* (2013.01); *A61B 2017/07285* (2013.01); *A61B 2018/00577* (2013.01); *A61B 2018/00595* (2013.01)

(58) Field of Classification Search
CPC ........... A61B 17/10; A61B 17/0643; A61B 2018/00595; A61B 2017/00221; A61B 2017/00398; A61B 2017/00734; A61B 2017/07285
USPC ........................................... 227/175.1–180.1
See application file for complete search history.

(56) References Cited

U.S. PATENT DOCUMENTS

| | | | |
|---|---|---|---|
| 4,840,563 A | 6/1989 | Altendorf | |
| 4,869,676 A | 9/1989 | Demler, Jr. et al. | |
| 5,093,593 A | 3/1992 | Philipp | |
| 5,433,721 A | 7/1995 | Hooven et al. | |
| 5,503,320 A | 4/1996 | Webster et al. | |
| 5,526,822 A | 6/1996 | Burbank et al. | |
| 5,608,771 A | 3/1997 | Steigerwald et al. | |
| 5,624,452 A | 4/1997 | Yates | |
| 5,667,517 A | 9/1997 | Hooven | |
| 5,752,644 A | 5/1998 | Bolanos et al. | |
| 5,769,211 A | 6/1998 | Manna et al. | |
| 5,779,130 A | 7/1998 | Alesi et al. | |
| 5,779,702 A | 7/1998 | Fard | |
| 5,827,323 A | 10/1998 | Klieman et al. | |
| 5,904,658 A | 5/1999 | Niederauer et al. | |
| 5,954,259 A | 9/1999 | Viola et al. | |
| 5,957,941 A | 9/1999 | Ream | |
| 6,045,564 A | 4/2000 | Walen | |
| 6,050,989 A | 4/2000 | Fox et al. | |
| 6,074,388 A | 6/2000 | Tockweiler et al. | |
| 6,096,004 A | 8/2000 | Meglan et al. | |
| 6,331,181 B1 | 12/2001 | Tierney et al. | |
| 6,471,659 B2 | 10/2002 | Eggers et al. | |
| 6,623,500 B1 | 9/2003 | Cook et al. | |
| 6,716,233 B1 | 4/2004 | Whitman | |
| 6,793,652 B1 | 9/2004 | Whitman et al. | |
| 6,846,307 B2 | 1/2005 | Whitman et al. | |
| 6,846,308 B2 | 1/2005 | Whitman et al. | |
| 6,846,309 B2 | 1/2005 | Whitman et al. | |
| 6,849,071 B2 | 2/2005 | Whitman et al. | |
| 7,003,351 B2 | 2/2006 | Tvaska et al. | |
| 7,032,798 B2 | 4/2006 | Whitman et al. | |
| 7,077,856 B2 | 7/2006 | Whitman | |
| 7,214,230 B2 | 5/2007 | Brock et al. | |
| 7,371,210 B2 | 5/2008 | Brock et al. | |
| 7,431,188 B1 | 10/2008 | Marczyk | |
| 7,565,993 B2 | 7/2009 | Milliman et al. | |
| 7,568,604 B2 | 8/2009 | Ehrenfels et al. | |
| 8,033,442 B2 | 10/2011 | Racenet et al. | |
| 8,393,513 B2 | 3/2013 | Jankowski | |
| 8,708,211 B2 * | 4/2014 | Zemlok ............ A61B 17/07207 227/175.1 |
| 8,800,837 B2 | 8/2014 | Zemlok | |
| 9,364,226 B2 * | 6/2016 | Zemlok ............ A61B 17/07207 |
| 2002/0128690 A1 | 9/2002 | Zarinetchi et al. | |
| 2003/0229344 A1 | 12/2003 | Dycus et al. | |
| 2004/0133189 A1 | 7/2004 | Sakurai | |
| 2004/0230214 A1 | 11/2004 | Donofrio et al. | |
| 2005/0059284 A1 | 3/2005 | Thurston et al. | |
| 2005/0095891 A1 | 5/2005 | Schorn | |
| 2005/0131390 A1 | 6/2005 | Heinrich et al. | |
| 2005/0177027 A1 | 8/2005 | Hirata | |
| 2005/0187576 A1 | 8/2005 | Whitman et al. | |
| 2005/0282102 A1 | 12/2005 | Kert | |
| 2005/0288739 A1 | 12/2005 | Hassler et al. | |
| 2005/0288743 A1 | 12/2005 | Ahn et al. | |
| 2006/0047271 A1 | 3/2006 | McPherson et al. | |
| 2006/0079865 A1 | 4/2006 | Jinno et al. | |
| 2006/0079879 A1 | 4/2006 | Faller et al. | |
| 2006/0148278 A1 | 7/2006 | Baily et al. | |
| 2006/0166548 A1 | 7/2006 | Williams et al. | |
| 2006/0212069 A1 | 9/2006 | Shelton | |
| 2006/0278680 A1 | 12/2006 | Viola et al. | |
| 2006/0289600 A1 | 12/2006 | Wales et al. | |
| 2007/0029363 A1 | 2/2007 | Popov | |
| 2007/0055304 A1 | 3/2007 | Whitman | |
| 2007/0102474 A1 | 5/2007 | Shelton et al. | |
| 2007/0137372 A1 | 6/2007 | Devengenzo et al. | |
| 2007/0149011 A1 | 6/2007 | Kent et al. | |
| 2007/0175949 A1 | 8/2007 | Shelton et al. | |
| 2007/0175956 A1 | 8/2007 | Swayze et al. | |
| 2007/0178767 A1 | 8/2007 | Harshman et al. | |
| 2007/0178768 A1 | 8/2007 | Harshman et al. | |
| 2007/0187456 A1 | 8/2007 | Viola et al. | |
| 2007/0270784 A1 | 11/2007 | Smith et al. | |
| 2007/0270790 A1 | 11/2007 | Smith et al. | |
| 2007/0270884 A1 | 11/2007 | Smith et al. | |
| 2007/0282335 A1 | 12/2007 | Young et al. | |
| 2008/0021440 A1 | 1/2008 | Solomon | |
| 2008/0041916 A1 | 2/2008 | Milliman et al. | |
| 2008/0103491 A1 | 5/2008 | Omori et al. | |
| 2008/0105730 A1 | 5/2008 | Racenet et al. | |
| 2008/0110960 A1 | 5/2008 | Jankowski | |
| 2008/0124951 A1 | 5/2008 | Cox et al. | |
| 2008/0142565 A1 | 6/2008 | Ehrenfels et al. | |
| 2008/0167736 A1 | 7/2008 | Swayze et al. | |
| 2008/0255607 A1 | 10/2008 | Zemlok | |
| 2008/0281353 A1 | 11/2008 | Aranyi et al. | |
| 2009/0270852 A1 | 10/2009 | Takashino et al. | |

FOREIGN PATENT DOCUMENTS

| | | | |
|---|---|---|---|
| WO | 0072765 A1 | 12/2000 | |
| WO | 03/026511 A1 | 4/2003 | |

OTHER PUBLICATIONS

European Search Report dated Jul. 28, 2011 for EP 11 15 2266.
European Office Action for EP 10250228.3 dated Apr. 29, 2015.
Canadian Office Action for CA 2,691,401 dated Feb. 23, 2016.

* cited by examiner

POWERED SURGICAL INSTRUMENT

CROSS-REFERENCE TO RELATED APPLICATIONS

The present application is a continuation of U.S. application Ser. No. 14/206,308, filed Mar. 12, 2014, now U.S. Pat. No. 9,364,226, which is a continuation of U.S. patent application Ser. No. 12/689,386, filed on Jan. 19, 2010, now U.S. Pat. No. 8,708,211, which claims the benefit of and priority to U.S. Provisional Application Ser. No. 61/152,051, filed on Feb. 12, 2009, the entire content of each of which is incorporated herein by reference.

TECHNICAL FIELD

The present disclosure relates generally to surgical instruments and, more specifically, to powered surgical instruments for engaging tissue.

BACKGROUND OF RELATED ART

Surgical instruments are well known in the art. Certain surgical instruments are used for applying parallel rows of staples through compressed living tissue. These surgical instruments are commonly employed for closing tissue or organs prior to transaction or resection, for occluding organs in thoracic and abdominal procedures, and for fastening tissue in anastomoses.

Typically, such surgical instruments include an anvil assembly, a cartridge assembly for supporting an array of surgical staples, an approximation mechanism for approximating the anvil and cartridge assemblies, and a firing mechanism for ejecting the surgical staples from the cartridge assembly. In some surgical instruments, the anvil and cartridge assemblies can jointly articulate or rotate with respect to the rest of the surgical instrument.

In use, a surgeon initially clamps tissue by approximating the anvil and cartridge members to each other. Next, the surgeon fires the instrument to place staples in the tissue clamped between the anvil and cartridge members. Optionally, the surgeon may use the same instrument or a separate instrument to cut the stapled tissue adjacent or between the row(s) of staples. Alternatively, the surgical instrument can sequentially eject the staples, while the anvil approximates the cartridge.

SUMMARY

The present disclosure relates to a powered surgical apparatus for engaging tissue. This powered surgical apparatus includes a handle assembly having proximal and distal portions, a movable portion operatively connected to the distal portion of the handle assembly, a tool assembly operatively coupled to the movable portion, a power source configured to supply electrical power, and a transmission system operatively associated with the power source. The movable portion is movable with respect to the handle assembly. The tool assembly is adapted to engage tissue. The transmission system is configured to transmit electrical power or signals between the handle assembly and the movable portion.

BRIEF DESCRIPTION OF FIGURES

Various embodiments of the presently disclosed surgical instrument are disclosed herein with reference to the drawings, wherein.

DETAILED DESCRIPTION

Figure 1:
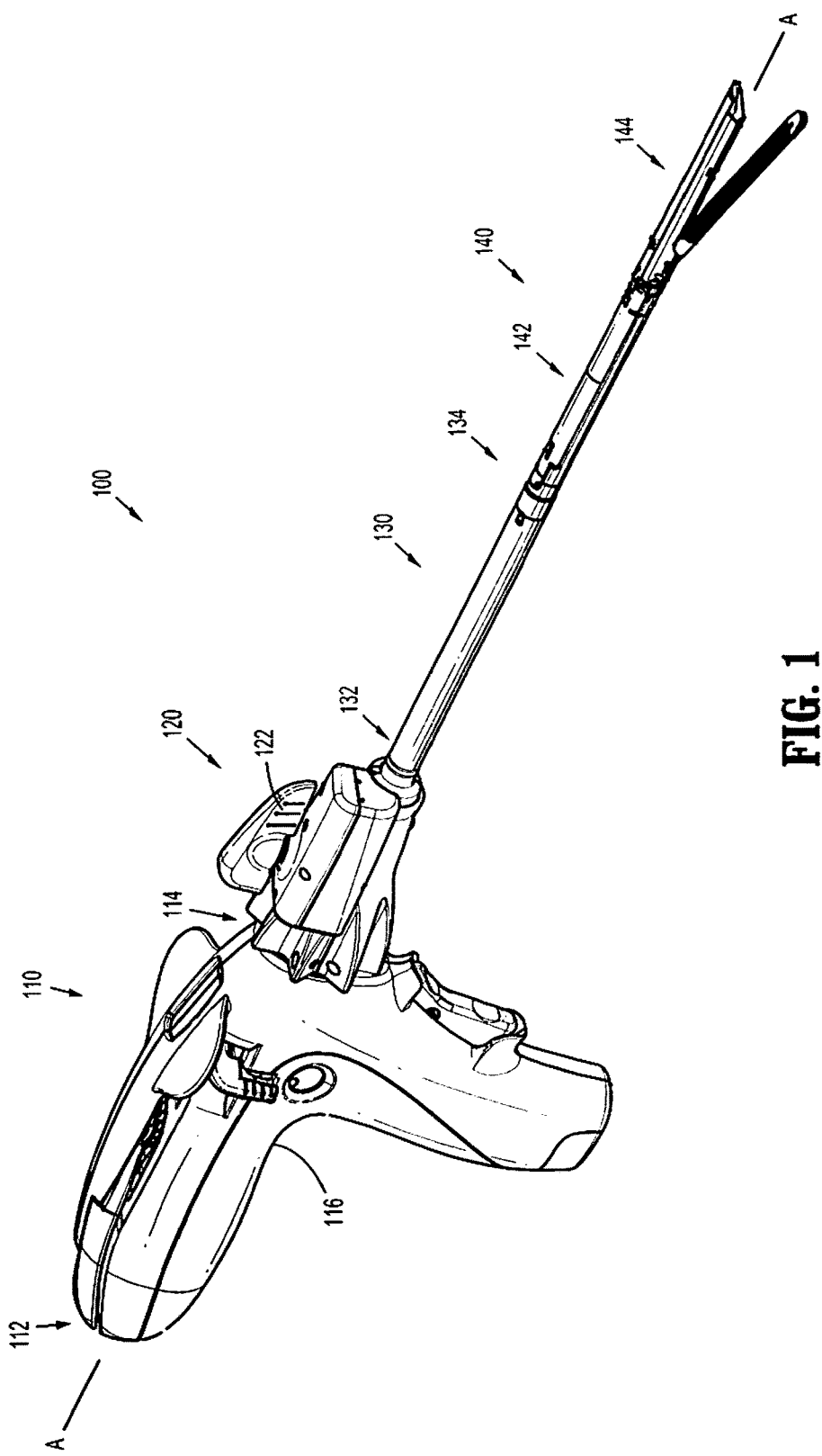
FIG. 1 is a perspective view of an embodiment of the surgical instrument of the present disclosure.

Embodiments of the presently disclosed powered surgical instrument are described in detail with reference to the drawings, wherein like reference numerals designate similar or identical elements in each of the several views. In the drawings and the description that follows, the term "proximal" refers to the end of the surgical instrument that is closer to the operator, whereas the term "distal" refers to the end of the surgical instrument that is farther from the operator. As appreciated by one skilled in the art, the depicted surgical instrument fires staples, but it may be adapted to fire any other suitable fastener such as clips and two-part fasteners. Additionally, the disclosed surgical instrument may include electrosurgical forceps or graspers. Commonly-owned patent application Ser. No. 10/369,894, filed on Feb. 20, 2003 (U.S. Patent Publication No. 2003/0229344), entitled VESSEL SEALER AND DIVIDER AND METHOD OF MANUFACTURING THE SAME, the entire contents of which are incorporated by reference herein, describes in detail a kind electrosurgical forceps.

With reference to FIG. 1, reference numeral 100 designates an embodiment of the presently disclosed surgical instrument. In the interest of brevity, the present disclosure focuses on a transmission system of surgical instrument 100. U.S. Patent Publication (USPP) Nos. 2008/0105730, filed on Nov. 28, 2007; USPPN 2008/0110960, filed on Jan. 8, 2008; USPPN 2008/0142565, filed on Jan. 24, 2008; USPPN 2008/0041916, filed on Oct. 15, 2007; U.S. Provisional Patent Application Ser. No. 61/050,273, filed on May 5, 2008; and U.S. patent application Ser. No. 11/786,198, filed on Apr. 10, 2007; Ser. No. 11/724,733, filed on Mar. 15, 2007; and U.S. patent application Ser. No. 11/786,933, filed on Apr. 13, 2007, describe in detail the structure and operation of surgical instruments that may incorporate the presently disclosed transmission system. The entire contents of these prior applications are incorporated herein by reference.

Surgical instrument 100 is configured to clamp, fasten, and/or cut tissue. Generally, surgical instrument 100 includes a handle assembly 110, a movable portion 120 adapted to move relative to handle assembly 110, an elongate portion 130 extending distally from movable portion 120 and defining a longitudinal axis "A-A," and a loading unit or tool assembly 140 adapted to engage tissue. Tool assembly 140 may include a various kinds of end effectors 144. Handle assembly 110 has proximal and distal portions 112, 114. Movable portion 120 extends distally from distal portion 114 of handle assembly 110 and is configured to rotate with respect to longitudinal axis A-A. Since movable portion 120 is operatively attached to elongate portion 130, rotating movable rotating portion 120 causes a corresponding rotation of elongate portion 130. Elongate portion 130 has proximal and distal ends 132, 134 and operatively interconnects handle assembly 110 and tool assembly 140. Tool assembly 140 includes a connecting section 142 releasably mounted onto distal end 134 of elongate portion 130 and an end effector 144.

End effector 144 may be adapted to clamp, fasten, cut, ablate, and/or cauterize tissue. In one embodiment, end effector is reusable. Alternatively, end effector 144 may be part of a disposable loading unit. U.S. Pat. No. 5,752,644, the entire contents of which are hereby incorporated by reference, describes in detail a disposable loading unit that can be incorporated to surgical instrument 100. In one embodiment, end effector 144 articulates with respect to longitudinal axis A-A upon movement of articulation knob 122 or actuation of an articulation switch 116 positioned on handle assembly 110.

Figure 2:
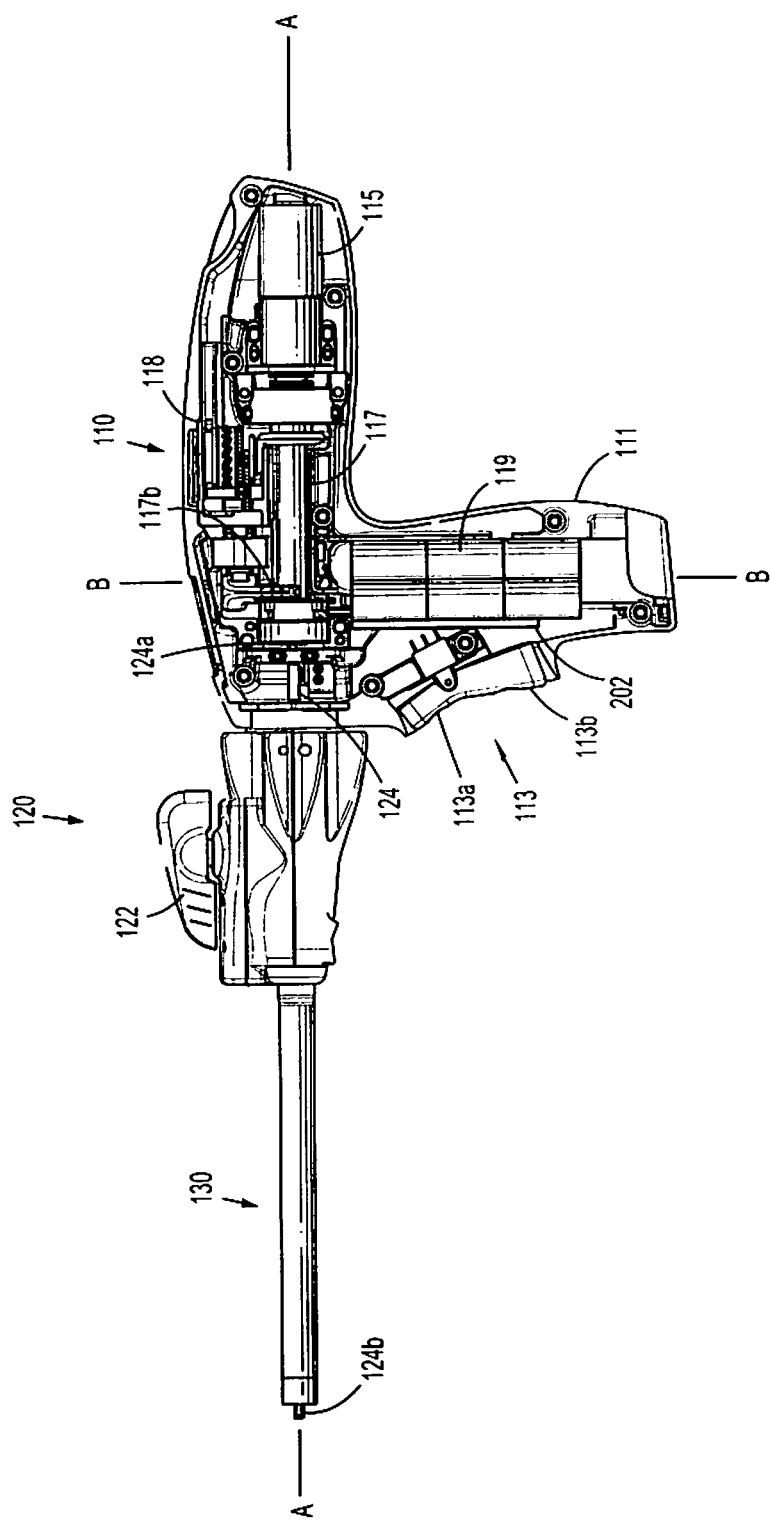
FIG. 2 is a side cross-sectional view of the surgical instrument of FIG. 1, showing the internal components thereof.
Figure 3:
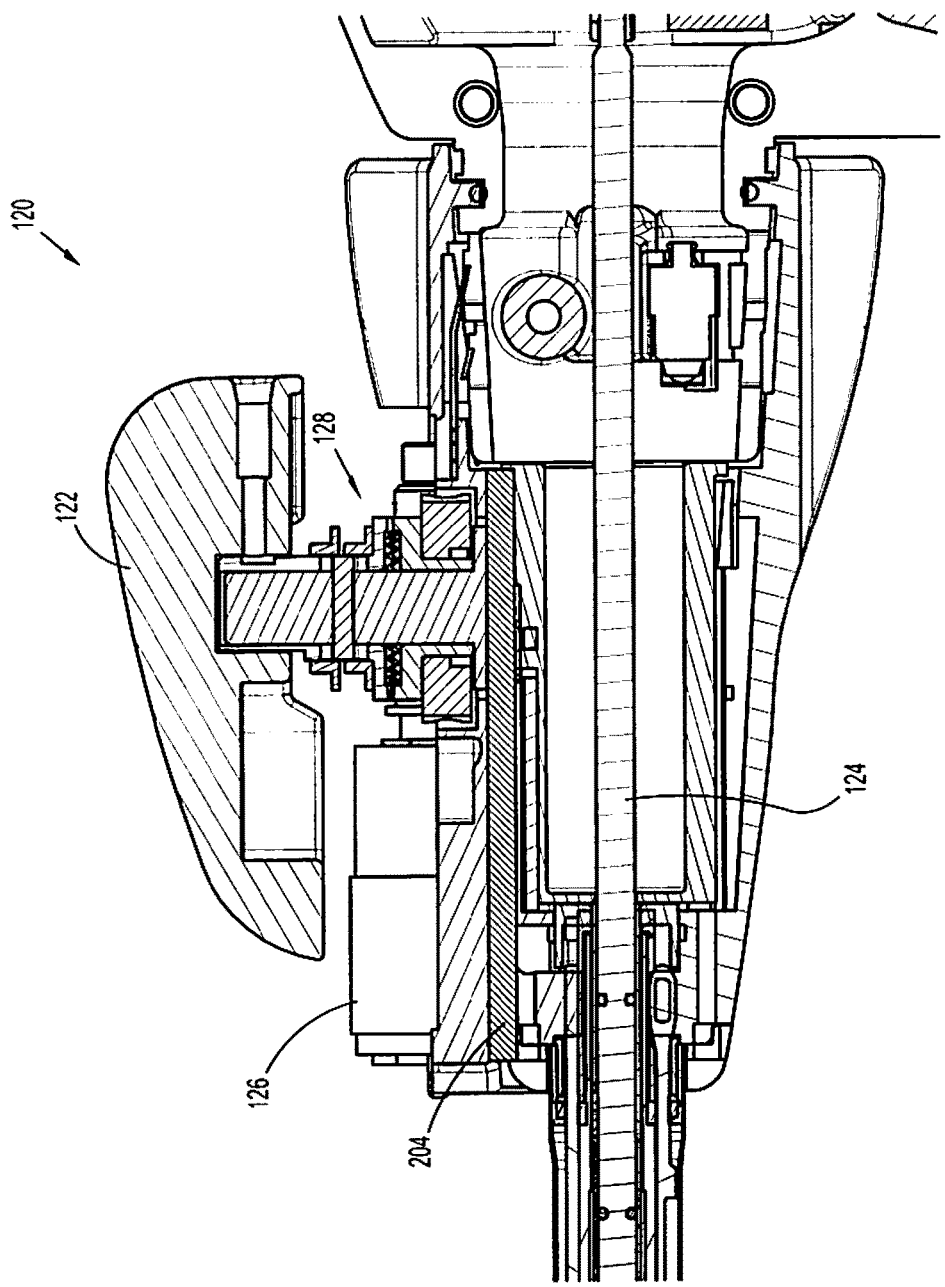
FIG. 3 is a side cross-sectional view of a movable portion of the surgical instrument of FIG. 1, showing the internal components thereof.

With reference to FIG. 2, handle assembly 110 includes a handle 111 and a housing 118. Handle 111 defines a longitudinal axis B-B and includes a switching mechanism 113 disposed thereon. Longitudinal axis B-B is substantially perpendicular to longitudinal axis A-A. As seen in FIG. 2, switching mechanism 113 may be a rocker switch having two switches 113a, 113b. Irrespective of its configuration, switching mechanism 113 starts and/or stops a first motor 115 when a user presses switch 113a or switch 113b. In one embodiment, switching mechanism 113 opens and closes an electrical circuit connecting a power source 119 to first motor 115. In another embodiment, first motor 115 starts and stops when the user presses switch 113a and second motor 126 (see FIG. 3) starts and stops when the user presses switch 113b. In this embodiment, the transmission system disclosed in detail below transmits signals or electrical power from power source 119 to second motor 126.

With continued reference to FIG. 2, housing 118 encompasses power source 119, first motor 115, and a drive tube 117. Power source 119 is electrically connected to first motor 115. In use, power source 119 supplies electrical power to first motor 115 when a user presses switch 113a or switch 113b. In the embodiment depicted in FIG. 2, power source 119 includes battery cells. Power source 119, however, may constitute any device, apparatus, or means capable of supplying electrical power. For example, power source 119 may include a battery pack, fuel cells, high-energy capacitors, or any combination thereof. In one embodiment, capacitors electrically connected to a battery pack form power source 119. Alternatively, surgical instrument 100 includes a cord connectable to an electrical energy generator.

Regardless of the kind of power source 119 employed, first motor 115 converts the electrical energy received from power source 119 into mechanical motion. First motor 115 is operatively associated with drive tube 117. During operation, drive motor 115 causes drive tube 117 to rotate about longitudinal axis A-A. While drive tube 117 rotates, it also translates between proximal and distal positions. A proximal end 124a of a firing rod 124 is attached to a distal end 117b of drive tube 117. Consequently, moving drive tube 117 longitudinally causes the longitudinal translation of firing rod 124. A portion of firing rod 124 is positioned within housing 118. Another portion of firing rod 124 extends through movable portion 120 and elongate portion 130. A distal end 124b of firing rod 124b is configured to be operatively connected to tool assembly 140. When tool assembly 140 is mounted to elongate portion 130, a longitudinal translation of firing rod 124 causes the actuation of end effector 144.

Housing 118 further contains a first board 202 that is part of a transmission system. The transmission system is adapted to transmit electrical power, control signals, feedback, sensing signal, or any combination thereof between first board 202 and a second board 204 disposed in movable portion 120. In one embodiment, the electrical power transmitted by transmission system stems from power source 119 (see FIG. 3). Control signals, feedback, sensing signals transferred by the transmission system originate from sensors, control systems, and feedback systems placed throughout surgical instrument 100.

Surgical instrument 100 includes sensors, control systems, and/or feedback systems located inside or outside handle assembly 110, movable portion 120, elongate portion 130 and/or tool assembly 140. Certain sensors, for instance, determine the operational stage of surgical instrument 100. Specifically, these sensors detect, among other things, articulation, rotation, clamping, and firing of end effector 144 or any other component of surgical instrument 100. Different types of sensors may be used in different ways to determine the operation stage of surgical instrument 100. For example, limit switches, proximity sensors, potentiometers, linear variable displacement transducer (LVDT), and/or shaft encoders may be employed to control and/or record the location of firing rod 124. Any of these sensors may also be used to detect a properly loaded staple cartridge. Moreover, electrical contacts, proximity sensors, optical sensors, RF sensors, magnetic sensors, photo diodes, and mechanical or metallic sensors may be used to control and/or record information concerning end effector 144. Furthermore, other sensors may monitor surgical instrument 100 to minimize the risk of overloading. For instance, thermal sensors, thermistors, thermopiles, thermo-couples, and thermal infrared imaging systems may monitor the temperature of first motor 115 or any other component of surgical instrument 100. In some embodiments, surgical instrument 100 includes an identification sensor for identifying the type of loading unit and/or staple cartridge loaded on surgical instrument 100. These identification sensors may include infrared, cellular chips, radiofrequency identification chips, microchips, emitters and transmitters located in tool assembly 140. These identification sensors communicate with first or second board 202, 204 or a receiver disposed therein. Some sensors transmit an electrical signal, whereas other sensors employ other means such as optics, lights, RF and magnets.

In addition to the sensors, some embodiments of surgical instrument 100 include systems, means, or devices for providing feedback to the user. For instance, display screens may be integral or separate from surgical instrument 100 for aiding the control of instrument 100. These display screens provide the user with useful information about operational characteristics of surgical instrument 100. Besides display screens, other feedback systems may be incorporated into surgical instrument 100. Some embodiments of surgical instrument 100 have pulsed patterns of lights, acoustic feedback (such as buzzers, bells or beeps sounded at selected time intervals), verbal feedback, and/or haptic vibratory feedback (such as asynchronous motor or solenoids). In certain embodiments, the visual, auditory or haptic feedback increases or decreases in intensity in response to a specific event, occurrence, or operational characteristic.

With reference to FIGS. 3-6, the transmission system, which include first and second boards 202, 204, serves as a conduit for control signals, feedback, sensing signals, and/or electrical power from the sensors, control systems, feedback systems, and/or power sources described above. In one embodiment, wires, leads, conductive strips, dielectric films, capacitors, cables, flexible conductors, conductive rings 121, or any other electrically conductive apparatus electrically interconnect first and second boards 202, 204. In the embodiment depicted in FIG. 4, movable portion 120 houses conductive rings 121 electrically coupling first board 202 to second board 204. Each conductive ring 121 has a pressure or cantilevered contacts 123 adapted to transfer electrical power, sensing signals, control signals, or feedback between first and second boards 202, 204. In use, cantilevered contacts 123 move and electrically close the circuit between power source 119 and second motor 126 when the user moves articulation knob 122 or triggers articulation switch 116.

Aside from second board 204, movable portion 120 contains a portion of firing rod 124, a second motor 126, and an articulation mechanism 128 for articulating end effector 144 with respect to longitudinal axis A-A. Articulation mechanism 128 is operatively coupled to second motor 126. Second motor 126 starts and/or stops when the user actuates articulation switch 116. Articulation mechanism 128 is also operatively connected to articulation knob 122. In operation, a user may articulate end effector 144 manually by moving articulation knob 122 or electromechanically by actuating articulation switch 116. End effector 144 articulates relative to longitudinal axis A-A upon actuation of articulation switch 116 or movement of articulation knob 122. The articulation of end effector 144 may be regulated or monitored with sensor or control systems transmitting signals, feedback, or data through either first or second boards 202, 204.

Figure 4:
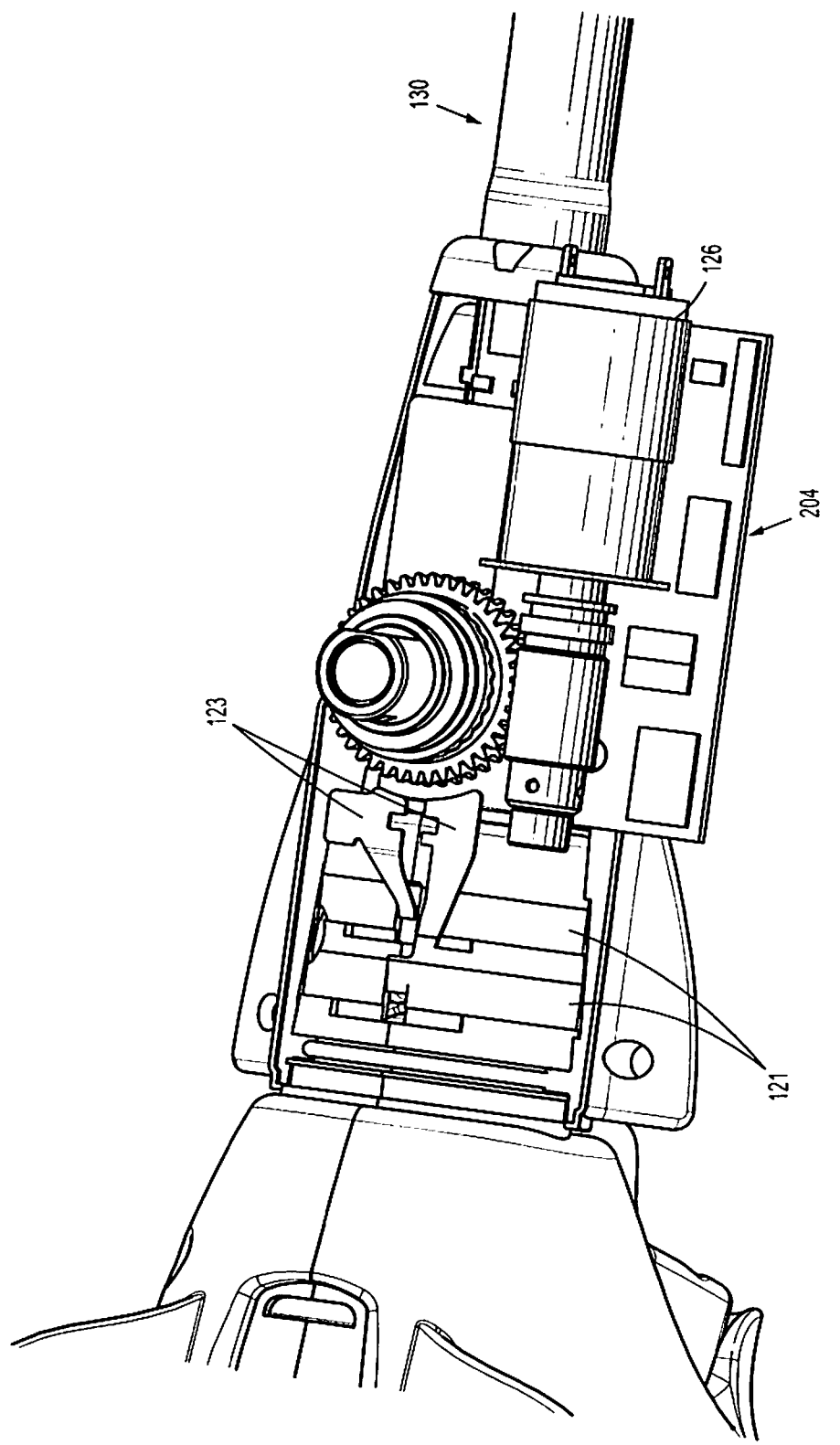
FIG. 4 is a perspective cut-away view of a portion of the surgical instrument of FIG. 1, showing the internal components of the movable portion.
Figure 5:
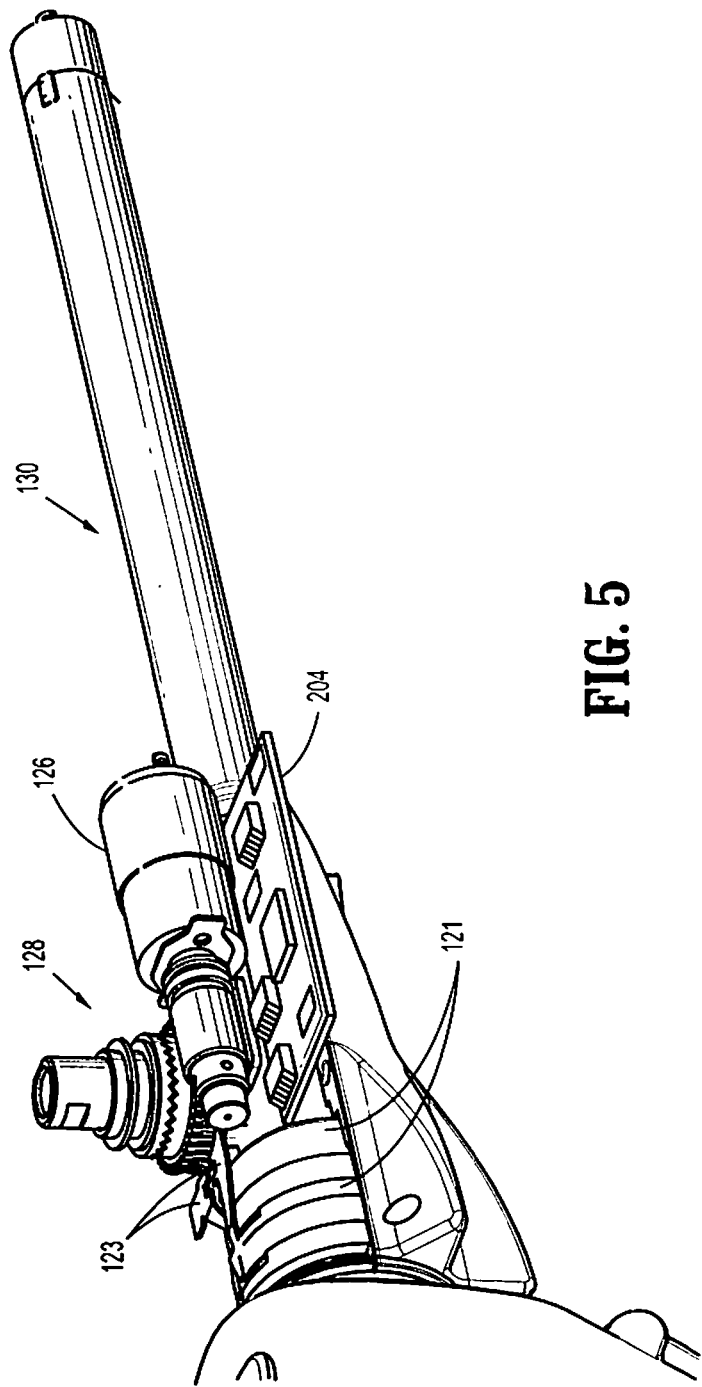
FIG. 5 is a perspective cut-away view of the movable portion and an elongate portion of the surgical instrument of FIG. 1, showing the internal components of the movable portion.
Figure 6:
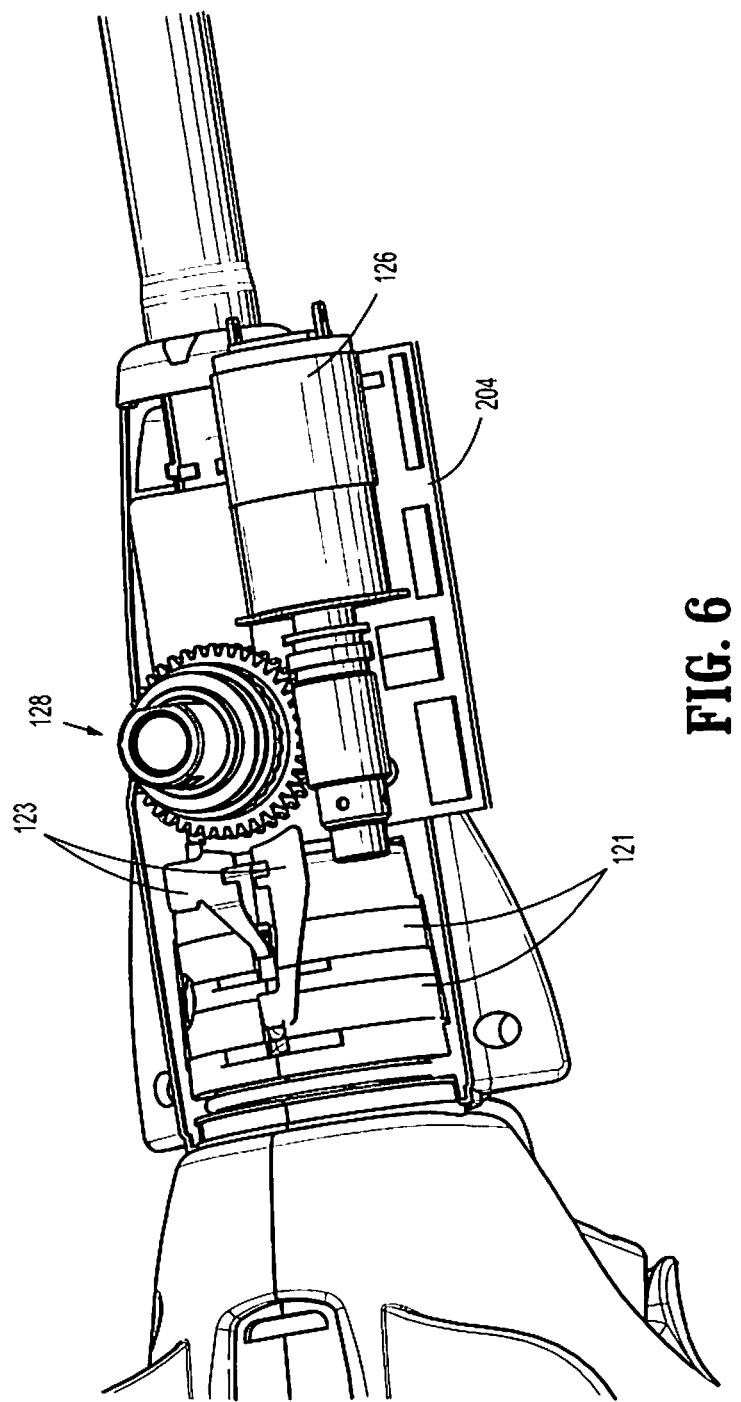
FIG. 6 is a perspective top cut-away view of the movable portion of the surgical instrument of FIG. 1, showing the internal components of the movable portion.

First and second boards 202, 204 include printed circuit boards, control circuits, electronic circuits, and/or inductive circuits. As seen in FIG. 4, second board 204 may be a printed circuit board. Second board 204 specifically includes a primary control circuit, a secondary control circuit, and/or a daughterboard. If second board 204 includes a primary control circuit, then first board 202 includes a secondary control circuit. Conversely, if first board 202 includes a primary control circuit, then second board 204 includes a secondary control circuit. In an embodiment where second board 204 includes a daughterboard, first board 202 includes a motherboard. In other embodiments, second board 204 constitutes a motherboard with a daughterboard mounted thereon. In this embodiment, the first board 202 may be a system or circuitry adapted to send electrical power, control signals, or feedback to second board 204. In certain embodiments, first board 202 communicates wirelessly with second board 204. Several means and systems may be used to transmit electrical power, signals, or information wirelessly from one board (202 or 204) to another.

As discussed above, second board 204 may include or function as a daughterboard in an embodiment of the present disclosure. In this embodiment, the daughterboard includes hardware and/or software for sensing, controlling, or providing feedback to the user. The sensing, controlling, and feedback functions of second board 204 can be performed while movable portion 120 remains stationary or during rotation or articulation of movable portion 120. Movable portion 120 can be rotated 360 degrees about longitudinal axis A-A and first board 202 is still able to communicate sensing signals, control signals, electrical power, and/or feedback to second board 204. In an embodiment, second board 204 includes a digital control module ("DCM") to control or monitor the operation of first and/or second motor 115, 126. In one embodiment, the DCM of second board 204 employs pulse-width modulation methods to control the output of first and/or second motors 115, 126. The second board 204 of this embodiment regulates the voltage or pulse-width modulates the voltage to adjust the electrical power and/or torque output to minimize the occurrences of system damage or to optimize electrical energy usage. In addition, an electric braking circuit may be incorporated in the DCM of second board 204 for controlling first or second motors 115, 126. In the case where second board 204 controls the operation of first motor 115, second board 204 relays a control or sensing signal to first board 202. In response to the control and sensing signals received from second board 204, first board 202 regulates or controls first motor 115. It is envisioned that the DCM of second board 204 may control or monitor other components of surgical instrument 100. Moreover, first board 202 may transfer electrical energy from power source 119 to second board 204. Alternatively, movable portion 120 may include another power source (supplementing or substituting power source 119) for supplying electrical power to second board 204. If surgical instrument 100 only has one power source located within movable portion 120, then second board 204 transmits electrical power wirelessly to first board 202. In the case that surgical instrument 100 has power source 119 and a second power source (not shown) positioned within movable handle 120, second board 204 may be partially or entirely powered by the second power source.

In another embodiment, first board 202 includes a primary control circuit and second board 204 contains a secondary control circuit. In the case where first board 202 includes a primary control circuit, second board 204 receives electrical power, control signals, feedback, and/or sensing signals from first board 202. Second board 204 then employs the electrical power, control signals, feedback, and/or sensing signals received from first board 202 to control, monitor, and/or drive second motor 126 or any other component of surgical instrument 100.

In the embodiment where second board 204 includes the primary control circuit and first board 202 includes the secondary control circuit, second board 204 transmits electrical power, control signals, feedback, and/or sensing signals to first board 202. First board 202 then utilizes the electrical power, control signals, feedback, and/or sensing signals received from the second board 204 to control, monitor and/or drive first motor 115 or any other component of surgical instrument 100.

As discussed above, an embodiment of surgical instrument 100 includes a power source (not shown) inside movable portion 120. This power source may substitute or supplement power source 119. If this power source substitutes power source 119, second board 204 transmits electrical power to first board 202 through a wireless connection, wires, capacitive conductors, leads, conductive rings 121, or any other form of electrical connection, to supply electrical power to first motor 115. In one embodiment, electrical power, control signals, sensing signals and feedback are transferred between first and second boards 202, 204 through inductive coupling. In this embodiment, each of first and second boards 202, 204 has an inductive circuit collectively forming an inductive interface. This inductive interface is configured to transfer electrical energy wirelessly between first and second boards 202, 204. The wireless electrical energy transfer between first and second boards 202, 204 may be used to power control circuits, send or receive signals, and/or drive motors 115, 126, solenoids, lasers, RF energy sources for tissue ablation or electrocautery systems. Moreover, the wireless electrical energy transfer may be employed to charge power sources (such as batteries and capacitors) located within movable portion 120. In embodiments where electrical energy is transferred wirelessly between first and second boards 202, 204, surgical instrument 100 does not necessarily need wires, cables, or contacts electrically connecting first and second boards 202, 204.

Data may also be transmitted between first and second boards 202, 204 through other means. In one embodiment, first board 202 includes a communication transmitter and second board 204 includes a receiver, or vice versa. The transmitter and receive may utilize any suitable protocol, standard, or technology for wirelessly transferring data, including, but not limited to, BLUETOOTH®, ANT3™, KNX™, Z WAVE™, X10™, wireless USB, WiFi™, IRDA™, NANONET™, TINY OS™, ZIGBEE™, radio, UHF, and VHF. Wireless energy transfer between first and second boards 202, 204 allows sensors utilizing light, optics, RF, magnetism, or other means that do employ electrical signals to be used within movable handle 120 without the need of wires or contacts. Second board 204, which is located inside movable portion 120, may include electronic circuits, or any other suitable device or system, to decipher the signals provided by these sensors.

It will be understood that various modifications may be made to the embodiments of the presently disclosed surgical instruments. Therefore, the above description should not be construed as limiting, but merely as exemplifications of embodiments. Those skilled in the art will envision other modifications within the scope and spirit of the present disclosure.

What is claimed is:

1. A powered surgical apparatus for engaging tissue, comprising:
    a first portion;
    a second portion rotatable about a longitudinal axis defined by the powered surgical apparatus; and
    a transmission system configured to transfer at least one of a signal or electrical power between the first and second portions, the transmission system including a first electronic board positioned in the first portion and a second electronic board positioned in the second portion, wherein the second electronic board is movable relative to the first electronic board while the first and second electronic boards are electrically coupled.

2. The powered surgical apparatus of claim 1, wherein the first portion has a first motor.

3. The powered surgical apparatus of claim 2, wherein the first electronic board controls the first motor in response to a control signal received from the second electronic board.

4. The powered surgical apparatus of claim 1, further comprising a tool assembly operatively coupled to the second portion.

5. The powered surgical apparatus of claim 1, wherein the first portion includes a handle assembly.

6. The powered surgical apparatus of claim 1, wherein the second portion includes a conductive ring electrically coupling the first electronic board to the second electronic board.

7. The powered surgical apparatus of claim 6, wherein the conductive ring has cantilevered contacts.

8. The powered surgical apparatus of claim 1, wherein the first electronic board includes a motherboard and the second electronic board includes a daughterboard.

9. The powered surgical apparatus of claim 1, wherein the first electronic board includes a primary control circuit and the second electronic board includes a secondary control circuit.

10. The powered surgical apparatus of claim 1, wherein the transmission system is configured to transmit control signals between the first and second electronic boards.

11. The powered surgical apparatus of claim 1, wherein the transmission system is configured to transmit feedback signals between the first and second electronic boards.

12. The powered surgical apparatus of claim 1, wherein the transmission system is configured to transmit electrical power wirelessly between the first and second portions.

13. A powered surgical apparatus for engaging tissue, comprising:
    a first portion;
    a second portion operatively coupled to a distal portion of the first portion, the second portion configured to rotate about a longitudinal axis defined by the powered surgical apparatus; and
    a transmission system including a first electronic board positioned in the first portion and a second electronic board positioned in the second portion, the second electronic board including a primary control circuit and a secondary control circuit, wherein the second electronic board is movable relative to the first electronic board while the transmission system transmits control signals between the first and second electronic boards.

14. The powered surgical apparatus of claim 13, wherein the second portion includes a conductive ring electrically coupling the first electronic board to the second electronic board.

15. The powered surgical apparatus of claim 13, wherein the conductive ring has cantilevered contacts.

16. The powered surgical apparatus of claim 13, wherein the first portion includes a first motor, wherein the first electronic board controls the first motor in response to a control signal received from the second electronic board.

17. The powered surgical apparatus of claim 13, further comprising a tool assembly operatively coupled to the second portion.

18. The powered surgical apparatus of claim 13, wherein the first portion includes a handle assembly.

\* \* \* \* \*